US00PP32182P3

(12) United States Plant Patent
Lyrene

(10) Patent No.: US PP32,182 P3
(45) Date of Patent: Sep. 15, 2020

(54) BLUEBERRY PLANT NAMED 'WAYNE'

(50) Latin Name: ***Vaccinium corymbosum* L.**
Varietal Denomination: WAYNE

(71) Applicant: Florida Foundation Seed Producers, Inc., Marianna, FL (US)

(72) Inventor: Paul M. Lyrene, Micanopy, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 16/350,891

(22) Filed: Jan. 29, 2019

(65) Prior Publication Data

US 2020/0015398 P1 Jan. 9, 2020

Related U.S. Application Data

(60) Provisional application No. 62/640,477, filed on Mar. 8, 2018.

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 5/08
See application file for complete search history.

(56) References Cited

U.S. PATENT DOCUMENTS

| | | | |
|---|---|---|---|
| PP10,675 | P | 11/1998 | Lyrene |
| PP11,807 | P2 | 3/2001 | Lyrene |
| PP12,165 | P2 | 10/2001 | Lyrene |
| PP16,404 | P3 | 4/2006 | Lyrene |
| PP26,312 | P2 | 1/2016 | Lyrene et al. |
| PP26,313 | P2 | 1/2016 | Lyrene et al. |
| PP26,523 | P3 | 3/2016 | Lyrene |
| PP26,679 | P2 | 5/2016 | Lyrene et al. |
| PP27,325 | P3 | 11/2016 | Lyrene |
| PP27,576 | P3 | 1/2017 | Lyrene |
| PP27,740 | P2 | 3/2017 | Norden et al. |
| PP27,771 | P2 | 3/2017 | Lyrene et al. |

OTHER PUBLICATIONS

U.S. Appl. No. 16/350,811, filed Jan. 15, 2019, Lyrene.
U.S. Appl. No. 16/350,892, filed Jan. 29, 2019, Lyrene et al.

*Primary Examiner* — Kent L Bell
(74) *Attorney, Agent, or Firm* — Dentons US LLP

(57) ABSTRACT

'WAYNE' is a new and distinct southern highbush blueberry (*Vaccinium corymbosum* L.) variety distinguished at least by a low chilling requirement, particularly for the flower buds; a vigorous, upright growth habit; good field disease resistance; earlier fruit ripening; and firm, sweet fruit that are medium to large in size and have small, dry picking scars.

2 Drawing Sheets

Latin name of the genus and species of the plant claimed: *Vaccinium corymbosum* L.

Variety denomination: 'WAYNE'.

BACKGROUND OF THE INVENTION

The present invention relates to a new and distinct hybrid variety of southern highbush blueberry (*Vaccinium corymbosum* L.) named 'WAYNE'. 'WAYNE' is a blueberry clone that can be distinguished at least by its low chilling requirement, particularly for the flower buds; good field disease resistance; and vigorous, upright growth habit. 'WAYNE' can also be distinguished at least by its berries that are medium to large in size, firm, and sweet. When grown in North-central Florida, 90% of the fruit are normally harvested between April 5 and May 5. 'WAYNE' has been asexually propagated by softwood stem cuttings in Gainesville and Waldo, Fla., and the resulting plants have all been phenotypically indistinguishable from the original plant.

'WAYNE' originated as a seedling from a cross between 'FL03-73' (unpatented) as the female (seed) parent and 'JEWEL' (U.S. Plant Pat. No. 11,807) as the male (pollen) parent. This cross was made in Gainesville, Fla. in February, 2003. The seedling was planted in a high-density field nursery in May, 2004, and the first fruit were evaluated in April, 2005. 'WAYNE' was first asexually propagated in Gainesville, Fla. by softwood stem cuttings in 2006. After the second year of fruiting in the field, in the spring of 2006, 'WAYNE' was propagated by softwood stem cuttings, and an experimental 15-plant test plot was established as part of a variety test at Windsor, Fla., in January, 2007. At this time, the experimental code 'FL06-354' was assigned to 'WAYNE'. Based on the growth, early yield, and fruit quality of this plot, 'WAYNE' was propagated by softwood stem cuttings and additional experimental test plots ranging from 5 to 45 plants were established in experimental research trials across Florida. These plots have been observed during flowering and ripening each year, and no mutations or off-type plants have been observed.

'JEWEL', is an important southern highbush blueberry variety that has been planted throughout the southeastern United States. 'WAYNE' exhibits a plant architecture that is similar to that of 'JEWEL', but with distinguishably less spreading. The leaves of 'WAYNE' are smaller in length and width compared to that of 'JEWEL'. Also 'WAYNE' produces earlier and firmer fruit than 'JEWEL'. 'WAYNE' also has higher early fruit yield than 'FL03-73', its female parent.

'WAYNE' is most similar to the southern highbush blueberry plant named 'Scintilla' (U.S. Plant Pat. No. 19,233). 'WAYNE' and 'Scintilla' are distinguishable at least in their flower arrangement and flower bud densities. Specifically, 'Wayne' exhibits flowers arranged alternately along a branch with leaves and exhibits high bud density. In contrast, 'Scintilla' exhibits flowers arranged alternately along a short, leafless, deciduous branch and exhibits medium bud density. Additionally, 'WAYNE' berries exhibit tight clusters, while 'Scintilla' berries exhibit loose clusters.

SUMMARY OF THE INVENTION

The following are characteristics of 'WAYNE' when grown under normal horticultural practices in Florida. 'WAYNE' exhibits a low chilling requirement, particularly for the flower buds; a vigorous, upright growth habit; good field disease resistance; earlier fruit ripening; and firm, sweet fruit that are medium to large in size and have small, dry picking scars.

BRIEF DESCRIPTION OF THE DRAWINGS

The accompanying photographs show typical bush, flower, and fruit characteristics for 'WAYNE'. Colors shown are as true as can be reasonably reproduced by photographic procedures and may differ from those cited in the detailed description, which accurately describes the colors of 'WAYNE'.

DETAILED BOTANICAL DESCRIPTION

Figure 1:
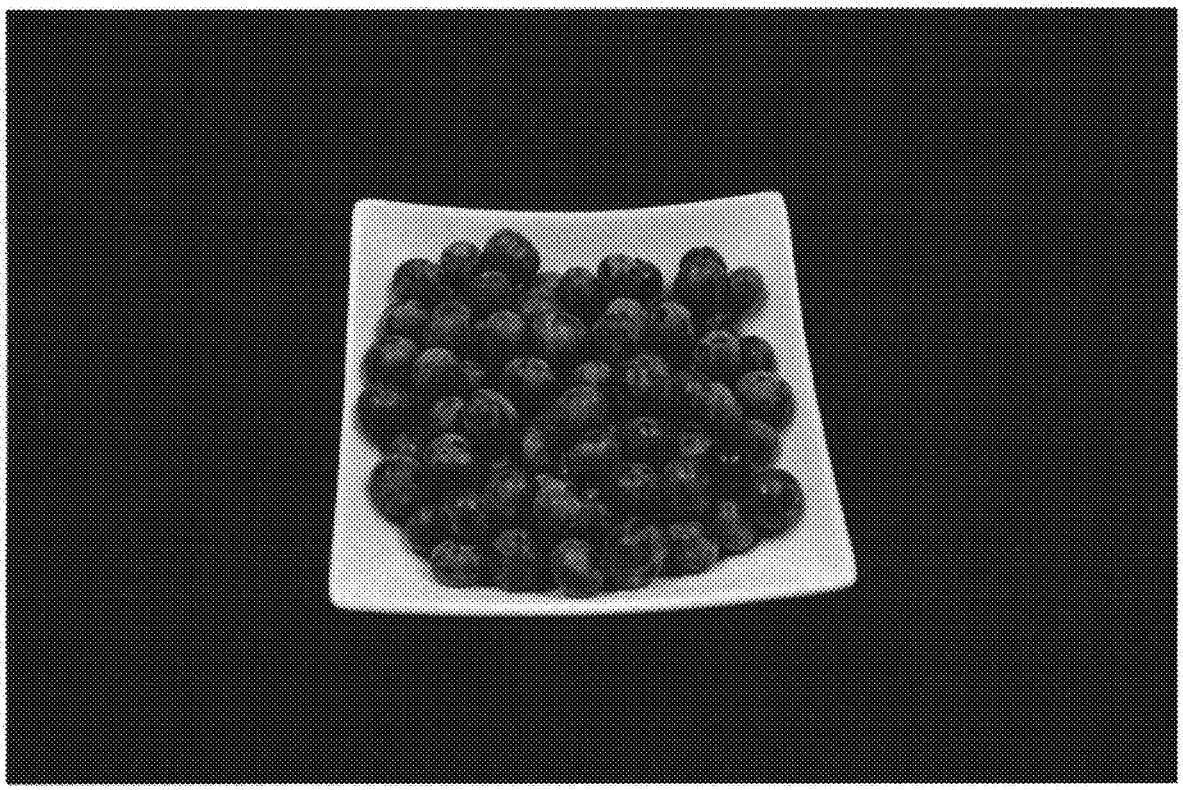
FIG. 1—Shows a close-up of harvested 'WAYNE' berries.
Figure 2:
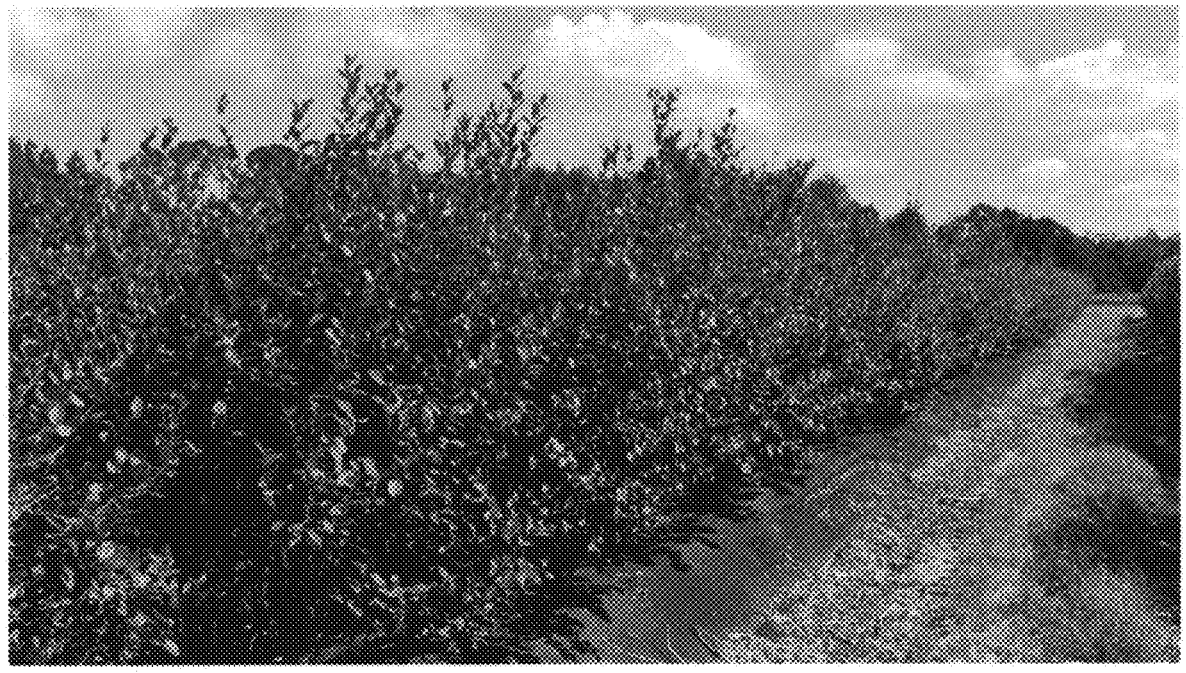
FIG. 2—Shows several five-year-old 'WAYNE' plants in October with the vigorous, semi-upright plant architecture visible.

The following detailed description sets forth distinctive characteristics of 'WAYNE'. The data that define these characteristics were collected from asexual reproductions carried out in Florida. The plant history was taken on a plot of plants growing in an experimental trial near Windsor, Fla. The plant was 5 years of age when the data was collected. Certain characteristics may vary with plant age. 'WAYNE' has not been observed under all possible environmental conditions, and the measurements given may vary when grown in different environments. Color descriptions are based on The Royal Horticultural Society (R.H.S.) Colour Chart by The Royal Horticultural Society, London, Fifth Edition, 2007. If any R.H.S. color designations below differ from the accompanying photographs, the R.H.S. color designations are accurate.

Classification:

*Family*.—Ericaceae.

*Botanical*.—*Vaccinium corymbosum* L.

*Common name*.—Southern Highbush Blueberry.

*Cultivar name*.—'WAYNE'.

Plant:

*Plant vigor*.—Medium to high.

*Growth habit*.—Upright.

*Plant height*.—1.80 m on average for 5-year-old plant.

*Plant spread*.—1.59 m on average for 5-year-old plant.

*Flower bud density* (*number*) *along flowering twigs in January*.—High.

*Twigginess*.—Medium.

*Tendency toward evergreenness*.—Medium.

*Productivity*.—In northeast Florida, 'WAYNE' produces 3-5 kg per season from plants 5 years old or older when hand harvested.

*Chilling requirement*.—200 hours below 7° C.

*Cold hardiness*.—'WAYNE' has been grown in temperate climates with extremely cold winter temperatures. Plants have survived winter freezes of −7° C. with minimal damage.

*Ease of propagation*.—'WAYNE' has only been propagated from softwood stem cuttings, where the rooting percentage is greater than 50% and comparable to other varieties.

Trunk and branches:

*Suckering tendency*.—Low-medium.

*Surface texture* (*of strong, 12-month-old shoots observed in October*).—Smooth.

*Surface texture* (*of 3-year-old and older wood*).—Rough.

*Color of new twigs observed in the field*.—Fan 3 153A yellow-green group.

*Color of 3-year-old, rough-textured canes*.—Fan 4 156A greyed brown group.

*Internode length* (*strong, upright shoots measured in June*).—Mean of 1.69 mm.

Leaves:

*Leaf arrangement*.—Alternate, Fibonacci Spiral

*Leaf veining*.—cross-venulate

*Length* (*including petiole, from tip of petiole to end of blade*).—Mean of 47.6 mm.

*Petiole length*.—Mean of 4.25 mm.

*Petiole diameter*.—Mean of 1.7136 mm.

*Width* (*at widest point*).—Mean of 26.3 mm.

*Leaf shape*.—Elliptic, with a small acute tip.

*Leaf base shape*.—Elliptic.

*Margin*.—Entire.

*Color*.—Upper surface: Fan 3 green group 137A. Lower surface: Fan 3 green group 138B. Leaf petiole color: Fan 3 yellow green group 150B.

*Pubescence*.—Upper surface of leaves: Absent. Lower surface of leaves: Absent. Margins: Absent.

*Timing of vegetative bud burst* (*early, medium, late*).—Medium.

*Relative time of leaving versus flowering*.—When not treated with hydrogen cyanamide in mid-winter, leafing occurs after flowering.

Flowers:

*Arrangement*.—Flowers are arranged alternately along a branch with leaves.

*Fragrance*.—Very slight floral fragrance.

*Shape*.—Urceolate and with slight radiations.

*Flowering period*.—Mean date of 40% open flowers in Waldo, Fla. is February 14; averages 10 days later than 'Emerald' (U.S. Plant Pat. No 12,165).

*Cluster*.—Tight.

*Number of flowers per cluster*.—Mean of 6.4.

*Pedicel*.—Length at time of anthesis: Mean of 4.7 mm. Color at time of anthesis: Fan 3 yellow-green group 144 D with Fan 2 red-purple group 63A on the sun exposed side..

*Peduncle*.—Length at time of anthesis: Highly variable; mean of 6.2 mm. Color at time of anthesis: Fan 3 yellow-green group 149D with Fan 2 red-purple group 58B on sun exposed side.

*Calyx*.—Surface texture: Smooth, no radiations, slight wax. Diameter: Mean of 6.6 mm. Color (outer surface, visible at the time of anthesis without removing the corolla tube): Fan 3 yellow-green group 144B with Fan 3 yellow-green 144D on tips of calyx lobes.

*Corolla*.—Diameter: mean of 7.7 mm. Length (from pedicel attachment point to corolla tip excluding the pedicel): Mean of 10.5 mm. Aperture diameter: Mean of 3.6 mm. Texture: Smooth with slight radiations. Color: Fan 4 white group NN155. Anthocyanin coloration in tube: Absent.

Reproductive organs:

*Style*.—Length (top of ovary to stigma tip): Mean of 8.2 mm. Color: Fan 3 yellow-green group N144D.

*Location of tip of stigma relative to lip of the corolla*.—Stigma tip is approximately even to 0.11 mm above the corolla tip.

*Anthers*.—Color: Fan 4 greyed-orange group 165B. Pollen: High. Pollen germination: Typically greater than 90%. Color: Fan 4 yellow-white group 158B. Filament length: 3.4 mm. Filament width: 1.1 mm.

*Self-fruitfulness*.—Low to medium. Planting in the field configurations that promote cross fertilization with other southern highbush varieties is recommended for all southern highbush blueberry plants grown in Florida.

Fruit:

*Mean date of* 50% *harvest in Citra, Fla*.—April 12.

*Diameter of calyx aperture on mature berry*.—Mean of 4.0 mm.

*Size and shape of calyx lobes on mature berry*.—Very small, Mostly erect to flat. Moderately Shallow calyx basin.

*Pedicel length on ripe berry*.—Mean of 6.2 mm.

*Detachment force for ripe berries* (*easy, medium, hard*) .—Medium.

*Fruit cluster density* (*sparse, medium, dense*).—Medium.

*Number of berries per cluster*.—Mean of 3.6.

*Fruiting type*.—On one-year-old shoots.

Berry:

*Cluster* (*tight, medium, loose*).—Tight.

*Weight* (*on well-pruned plants*).—Mean of 2.2 g.

*Height*.—Mean of 14.2 mm.

*Width*.—Mean of 17.3 mm.

*Shape*.—Mostly circular to partial oblate.

*Surface color of mature berries ripe on the plant*.—Fan 2 violet-blue group 96D.

*Intensity of fruit bloom*.—High.

*Surface color of ripe berry after polishing*.—Fan 4 black group 203B.

*Immature berry color, with bloom*.—Fan 3 yellow-green group 145D.

*Immature berry color, without bloom*.—Fan 3 yellow-green group 145C.

*Flesh color*.—Fan 4 green-white group 157C.

*Surface wax*.—High. The surface wax on 'Wayne' has medium persistence.

*Pedicel scar*.—Small and dry.

*Firmness*.—Firm. Mean 177.21 g/mm.

*Flavor*.—Sweet, with some acid hints.

*Intensity of fruit sweetness*.—Medium to High.

*Texture*.—Good texture, and no stone cells present.

*Fruit storage quality*.—Fruit is firm and can be stored without shriveling, mold or loss of firmness for 2 weeks at 4° C.

Seeds:

*Color of dried seeds*.—Fan 4 greyed orange group 165B.

*Weight of* 25 *well-developed dried seed*.—Mean of 10.6 mg.

*Length of well-developed dried seeds*.—Mean of 1.692 mm.

*Width of well-developed dried seeds*.—Mean of 0.752 mm.

Use: 'WAYNE' produces southern highbush blueberries suitable for both the fresh and processed fruit markets.

Resistance to diseases, insects, and mites: 'WAYNE' has grown vigorously and shows excellent bush survival in the field. It appears to be tolerant to stem blight (*Botryosphaeria* spp.) and root rot (*Phytophthora cinnamoni*), with almost no young plants dying soon after planting. Among all selections, 'WAYNE' is within the 3% that exhibit 95% of its plants surviving for at least 8 years when planted in a high disease fields. The reaction of 'WAYNE' to the various fungal species that cause summer leaf spots is typical of other southern highbush varieties, and fungicide applications may be needed after harvest to reduce foliar diseases and retain leaves into the fall for maximum flower bud set. Susceptibility to typical blueberry insect and mite pathogens such as spotted wing drosophila (*Drosophila suzukii*), blueberry gall midge (*Dasineura oxycoccana*), and blueberry bud mite (*Acalitus vaccini*) is similar to other southern highbush cultivars.

What is claimed is:

1. A new and distinct variety of southern highbush blueberry plant named 'WAYNE', as illustrated and described herein.

* * * * *